US008066987B2

(12) United States Patent  
Moore et al.

(10) Patent No.: US 8,066,987 B2  
(45) Date of Patent: Nov. 29, 2011

(54) BACTERIAL DELIVERY OF BIOLOGICALLY ACTIVE POLYPEPTIDES

(75) Inventors: Robert John Moore, Ascot Vale (AU); Julian Ian Rood, Bentleigh (AU); Scott Andrew Sheedy, North Geelong (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 709 days.

(21) Appl. No.: 12/064,947

(22) PCT Filed: Aug. 29, 2006

(86) PCT No.: PCT/AU2006/001255  
§ 371 (c)(1),  
(2), (4) Date: Jul. 15, 2008

(87) PCT Pub. No.: WO2007/025333  
PCT Pub. Date: Mar. 8, 2007

(65) Prior Publication Data  
US 2009/0022691 A1    Jan. 22, 2009

Related U.S. Application Data

(60) Provisional application No. 60/712,136, filed on Aug. 30, 2005.

(51) Int. Cl.  
*A01N 63/00* (2006.01)
(52) U.S. Cl. ........................................ 424/93.4
(58) Field of Classification Search ................ None  
See application file for complete search history.

(56) References Cited

U.S. PATENT DOCUMENTS

| | | |
|---|---|---|
| 6,605,286 B2 | 8/2003 | Steidler et al. |
| 6,746,671 B2 | 6/2004 | Steidler et al. |
| 6,866,847 B1 | 3/2005 | Kelly-Aehle |
| 2004/0170639 A1 | 9/2004 | Kelly-Aehle |

FOREIGN PATENT DOCUMENTS

| | | |
|---|---|---|
| EP | 0413378 A1 * | 7/1990 |
| EP | 0413378 | 1/1995 |
| WO | WO00/04919 | 2/2000 |
| WO | WO01/19974 | 3/2001 |

OTHER PUBLICATIONS

Zhu, Delivery of heterologous protein antigens via hemolysin or autotransporter systems by an attenuated ler mutant of rabbit enteropathogenic *Escherichia coli*, Center for Vaccine Development, University of Maryland School of Medicine, 685 West Baltimore Street, Baltimore, MD 21201, USA, pp. 1-11, 2005.
Castagliuolo, Engineered *E. coli* delivers therapeutic genes to the colonic mucosa, Department of Histology, Microbiology and Medical Biotechnologies, University of Padua, Padua, Italy, Gene therapy, 12, pp. 1070-1078, 2005.
Lui, Expression of Rumen Microbial Fibrolytic Enzyme Genes in Probiotic *Lactobacillus reuteri*, Applied and Environmental Microbiology, Nov. 2005, p. 6769-6775, vol. 71, No. 11.
Huyghebaert, et al, Development of an enteric-coated formulation containing freeze-dried, viable recombinant *Lactococcus lactis* for the ileal mucosal delivery of human interleukin-10, European Journal of Biopharmaceuticals, Aug. 2005;60(3):349-359.
Roland, Recent advances in the development of live, attenuated bacterial vectors, Current Opinion in molecular therapeutics, (1):62-72, Jul. 1, 2005.
Ingham, A versatile system for the expression of nonmodified bacteriocins in *Escherichia coli*, Journal of Applied Microbiology, 2005;98(3):676-683.
Mergulha, Recombinant protein secretion in *Escherichia coli*, Biotechnology Advances, vol. 23, Issue 3, May 2005, pp. 177-202.
Prakash, Artificial Cell Therapy: New Strategies for the Therapeutic Delivery of Live Bacteria, Biomed Biotechnol. 2005; 2005(1): 44-56.
Palacios, Characterization of an acid phosphatase from *Lactobacillus pentosus*: regulation and biochemical properties, Journal of Applied Microbiology, vol. 98, No. 1, Jan. 2005 , pp. 229-237(9).
Choi, Secretory and extracellular production of recombinant proteins using *Escherichia coli*, Applied Microbiology and Biotechnology, vol. 64, No. 5, Jun. 2004 , pp. 625-635(11).
Kimoto, New *Lactococcus* strain with immunomodulatory activity: enhancement of Th1-type immune response, Microbiology Immunology, 2004;48(2):75-82.
Boman, Antibacterial peptides: basic facts and emerging concepts, Journal of Medicine, Sep. 2003;254(3):197-215.
Steidler, Biological containment of genetically modified *Lactococcus lactis* for intestinal delivery of human interleukin 10, Nature Biotechnology, Jul. 2003;21(7):785-9. Epub Jun. 15, 2003.
Bermudez, Intranasal Immunization with Recombinant *Lactococcus lactis* Secreting Murine Interleukin-12 Enhances Antigen-Specific Th1 Cytokine Production, Infect Immun. Apr. 2003; 71(4): 1887-1896.
Ingham, The bacteriocin piscicolin 126 retains antilisterial activity in vivo, Journal of Antimicrobial Chemotherapy vol. 51, No. 6, pp. 1365-1371, 2003.
Vohra, Phytases: Microbial sources, production, purification, and potential biotechnological applications, Critical Reviews in Biotechnology, pp. 29-60, Mar. 1, 2003.
Garmory, The use of live attenuated bacteria as a delivery system for heterologous antigens, Journal of Drug Targeting, 2003;11(8-10):471-479.
Cullen, Construction and evaluation of a plasmid vector for the expression of recombinant lipoproteins in *Escherichia coli*, Plasmid 49, Jan. 2003;49(1):18-29.

(Continued)

*Primary Examiner* — Gary B. Nickol  
*Assistant Examiner* — Khatol Shahnan-Shah  
(74) *Attorney, Agent, or Firm* — Carol L. Francis; Bozicevic, Field & Francis LLP

(57) ABSTRACT

The present invention relates to methods for the delivery of biologically active polypeptides to a subject by colonizing non-pathogenic Gram negative bacteria. Also provided by this invention are methods of treating or preventing diseases by administering colonizing Gram negative bacteria that express one or more biologically active polypeptides. The colonizing non-pathogenic Gram negative bacteria may be administered in pharmaceutical formulations.

17 Claims, 13 Drawing Sheets

OTHER PUBLICATIONS

Figure 1:
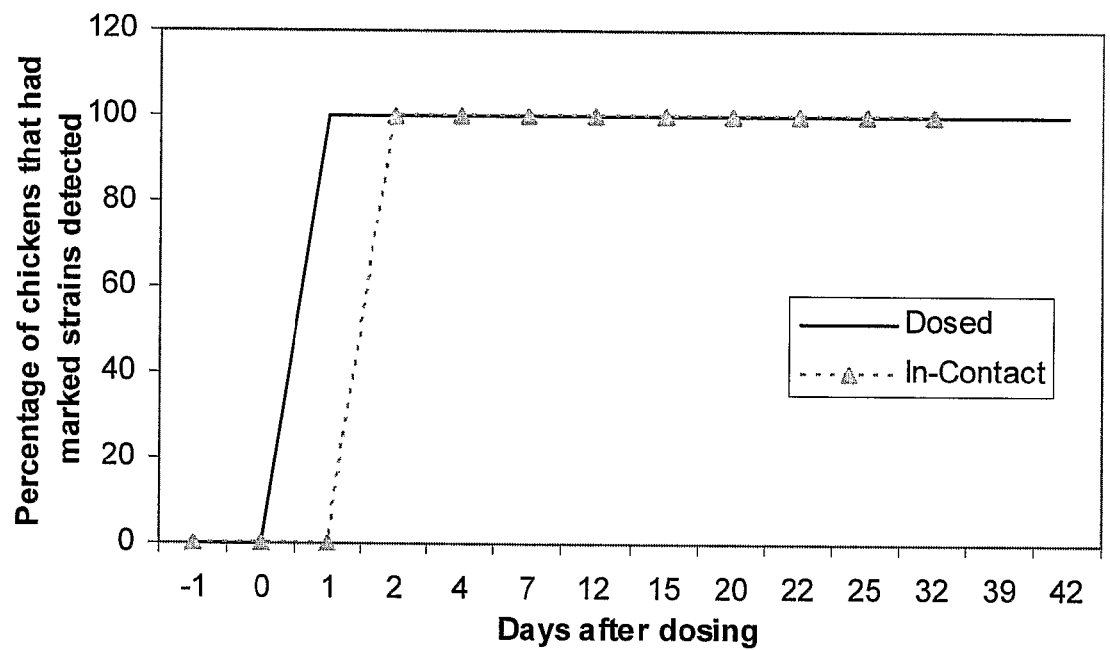

Steidler, in situ delivery of cytokines by genetically engineered *Lactococcus lactis*, vol. 82, Nos. 1-4, Aug. 2002, pp. 323-331(9).

King, Tumor-Targeted Salmonella Expressing Cytosine Deaminase as an Anticancer Agent, Human Gene Therapy. Jul. 1, 2002, 13(10): 1225-1233.

Medina, Use of live bacterial vaccine vectors for antigen delivery: potential and limitations, Vaccine, vol. 19, Feb. 8, 2001, pp. 1573-1580.

Cho, Expression of *Clostridium thermocellum* endoglucanase gene in *Lactobacillus gasseri* and *Lactobacillus johnsonii* and characterization of the genetically modified probiotic *Lactobacilli*, Current microbiology, vol. 40, pp. 257-263, 2000.

Ennahar, Class IIa bacteriocins : biosynthesis, structure and activity, FEMS microbiology reviews, 2000, vol. 24, pp. 85-106.

Kalhusdal, Necrotic enteritis challenge models with broiler chickens raised on litter: evaluation of preconditions, *Clostridium perfringens* strains and outcome variables, Femms Immunology and Medical Microbiology 24, (1999) 337-343.

Craven, Cecal carriage of *Clostridium perfringens* in broiler chickens given Mucosal Starter Culture, Avian Diseases, Jul.-Sep. 1999;43(3):484-90.

Saltzman, Patterns of hepatic and splenic colonization by an attenuated strain of *Salmonella typhimurium* containing the gene for human interleukin-2: a novel anti-tumor agent, Cancer Biotherapy & Radiopharmaceuticals, Feb. 1997;12(1):37-45.

Bhugaloo-Vial, Purification and amino acid sequences of piscicocins V1a and V1b, two class IIa bacteriocins secreted by *Carnobacterium piscicola* V1 that display significantly different levels of specific inhibitory activity, Appl. Environ. Microbiol., Dec. 1996, 4410-4416, vol. 62, No. 12.

Jack, Bacteriocins of gram-positive bacteria, Microbiol Rev. Jun. 1995; 59(2): 171-200.

Boman, Peptide antibiotics and their role in innate immunity, Annual Review of Immunology, 1995;13:61-92.

Nahashon, Phytase activity, phosphorus and calcium retention, and performance of single comb White Leghorn layers fed diets containing two levels of available phosphorus and supplemented with direct-fed microbials, Poltry Science, Oct. 1994;73(10):1552-62.

Devriese, in vitro susceptibility of *Clostridium perfringens* isolated from farm animals to growth-enhancing antibiotics, Journal of Applied Bacteriology, Jul. 1993;75(1):55-7.

Tacket, Clinical acceptability and immunogenicity of CVD 908 *Salmonella typhi* vaccine strain, Vaccine, vol. 10, 1992;10(7):443-6.

Tschirdewahn, The presence of enterotoxigenic *Clostridium perfringens* strains in faeces of various animals, International Journal of Food Microbiology, Nov. 1991;14(2):175-8.

Gabay, Antibiotic proteins of human polymorphonuclear leukocytes, Proc Natl Acad Sci U S A. Jul. 1989; 86(14): 5610-5614.

Soravia, Antimicrobial properties of peptides from Xenopus granular gland secretions, Federation of European Biochemical Societies Feb. 15, 1988;228(2):337-340.

Cowan, Experimentally Induced Necrotic Enteritis in Chickens, Avian Diseases 31,:904-906, 1987.

Kondo, In vitro lecithinase activity and sensitivity to 22 antimicrobial agents of *Clostridium perfringens* isolated from necrotic enteritis of broiler chickens, Research in Veterinary Science, Nov. 1988;45(3):337-340.

Tagg, Bacteriocins of gram-positive bacteria, American Society for Microbiology, Sep. 1976, 9p. 722-756.

Agars, isolation of *shigella*, The American Journal of clinical pathology, 1965, vol. 44, No. 4.

Hektoen, New culture medium for the isolation of *Bacillus typhosus* from stools, the journal of infectious diseases, vol. 18, 1916.

Alfred MacConkey, Lactose-fermiting bacteria in faeces, The journal of hygiene, vol. 5, No. 3, pp. 333-379, Jul. 1905.

Curtiss III; et al., "Nonrecombinant and recombinant avirulent Salmonella vaccines for poultry", Veterinary Immunology and Immunopathology (1996), 54:365-372.

Kulkarni; et al., "Oral immunization of broiler chickens against necrotic enteritis with an attenuated Salmonella vaccine vector expressing Clostridium perfringens antigens", Vaccine (2008), 26:4194-4203.

"Supplementary European Search Report", European Patent Office, Apr. 24, 2009, 06774884.8-2403 / 1934349.

Weiss; et al., "Bacteria-Mediated Transfer of Eukaryotic Expression Plasmids into Mammalian Host Cells", Biol. Chem. (2001), 382:533-541.

Weiss; et al., "Transfer of eukaryotic expression plasmids to mammalian host cells by bacterial carriers", Current Opinion in Biotechnology (2001), 12(5):467-472.

Westendorf; et al., "Intestinal immunity of *Escherichia coli* NISSLE 1917: a safe carrier for therapeutic molecules", FEMS Immunology and Medical Microbiology (2005) 43:373-384.

Van Immerseel; et al., "Rethinking our understanding of the pathogenesis of necrotic enteritis in chickens", Trends in Microbiology (2009), 17(1):32-36.

* cited by examiner

BACTERIAL DELIVERY OF BIOLOGICALLY ACTIVE POLYPEPTIDES

FIELD OF THE INVENTION

The present invention relates to colonising Gram negative bacterial strains. The invention relates in particular to live colonising Gram negative bacteria and their use for in vivo delivery of biologically active proteins.

BACKGROUND OF THE INVENTION

The delivery of gene products, such as proteins and RNA, to animals or animal cells is desirable for a variety of applications. Such applications include treatment of infectious diseases, therapy of acquired or inherited diseases or conditions, induction of an immune response to a protein antigen, the study of various cellular functions, etc. A range of bacteria have therefore been developed and used for the delivery of therapeutic molecules.

For example, live, attenuated, pathogenic Gram negative bacteria have been developed as vaccines (Garmory et al., 2003). Furthermore, strategies have been developed to use live, attenuated, pathogenic Gram negative bacterial vaccine strains as vectors to deliver a variety of protective vaccine antigens via the mucosal route (Medina, 2001; Roland et al., 2005). Such strains are generally non-colonising.

Gram positive, non-pathogenic lactic acid bacteria are also currently being developed as oral live vaccines (Bermudez-Humaran et al., 2003). In contrast to the attenuated, pathogenic Gram negative bacterial strains, Gram positive bacteria, such as *Lactococcus lactis*, are non-pathogenic. Furthermore, the Gram positive bacterial vectors often have a limited ability to colonise. In addition to delivering vaccine antigens, *L. lactis* is also being developed for the delivery of a number of cytokines such as IL-10 (Steidler, 2002; Steidler et al., 2003; Huybhebaert et al., 2005), IL-12 (Bermudez-Humaran et al., 2003; Kimoto et al., 2004) and IL-2 (Steidler, 2002). Methods for the delivery of surface anchored proteins by Gram positive bacteria are disclosed in U.S. Pat. No. 6,737,521, and methods for the delivery of cytokines in *L. lactis* are described in U.S. Pat. No. 6,605,286.

Live bacterial vectors are also potentially useful in the treatment of infectious diseases. For example, live bacterial vectors are potentially useful in the treatment of infectious diseases such as necrotic enteritis. Necrotic enteritis is an enterotoxemic disease caused by *Clostridium perfringens* which leads to the development of necrotic lesions in the gut wall resulting in morbidity and mortality of poultry. It is also a multifactorial disease with complex and partly unknown epidemiology and pathogenesis (Kaldhusdal, 1999). The bacterium, *C. perfringens* is commonly found in the gastrointestinal tract of poultry (Tschirdewahn et al. 1991), the occurrence of necrotic enteritis, however, is sporadic (Cowen et al., 1987). Nevertheless, feed contaminated with *C. perfringens* has been implicated in outbreaks of necrotic enteritis in chickens (Kaldhusdal, 1999). Studies have also shown that healthy chickens have a relatively low number of *C. perfringens* in their gastrointestinal tracts, while an increase in the concentration of the bacteria can result in a necrotic enteritis condition (Craven et al., 1999).

Bacitracin, linocomycin and other antibiotics have been commonly used to treat poultry suffering from necrotic enteritis (Craven et al., 1999). However, due to the isolation of antibiotic-resistant strains of *C. perfringens* from chickens and turkeys (Devriese et al., 1993; Kondo, 1988; Watkins et al., 1997) and the general desire to reduce antibiotic use because of the potential link to antibiotic resistance in human pathogens, poultry health authorities and producers are increasingly interested in the development and application of new products to replace traditional antibiotics. To date, however, there have been no reports of the treatment of necrotic enteritis using live rationally designed bacterial vectors delivering therapeutic products. However, there have been reports of the use of probiotic strains of bacteria and the use of largely uncharacterised single isolates and mixed populations of bacteria for competitive exclusion treatments.

Despite having great potential, the live bacterial vectors used to date, in other systems, have substantial limitations. For example, when given orally, bacterial cells are exposed to harsh gastrointestinal conditions, resulting in short survival time and requiring that a large dose be given (Prakash and Jones, 2005). A consequence of clearance of the bacteria from a subject is that delivery of the biologically active protein is of limited duration. An additional problem associated with the use of attenuated Gram negative bacterial vectors has been the difficulty in obtaining a balance between residual virulence of invasive and/or reactogenic vectors (Tacket et al., 1992) and the effective delivery of the bioactive polypeptide, such as a immunogenic construct (Zhu et al., 2006).

Accordingly, there is a need for improved bacterial vectors that are not hindered by these limitations.

SUMMARY OF THE INVENTION

The present inventors have now isolated novel colonising Gram negative bacterial strains that are useful for delivering biologically active proteins to a subject. These colonising bacterial strains enable the delivery of biologically active proteins to particular sites in the subject where the biologically active protein is required.

Accordingly, the present invention provides a method of delivering one or more heterologous biologically active polypeptides to a subject, the method comprising administering to the subject a colonising non-pathogenic Gram negative bacterium that expresses one or more heterologous biologically active polypeptides.

In one embodiment, the bacterium is *E. coli*. Preferably, the *E. coli* has the serotype H antigen, H10. In a preferred embodiment, the *E. coli* is a strain selected from CCEC22 as deposited with the National Measurement Institute (formerly AGAL) under accession number NM05/45635, CCEC31 as deposited with the National Measurement Institute (formerly AGAL) under accession number NM05/45636 or CCEC59 as deposited with the National Measurement Institute (formerly AGAL) under accession number NM05/45637 which has been modified to express one or more heterologous biologically active polypeptides.

In another embodiment, the bacterium is a strain of *Salmonella*. Preferably, the strain is *S. enterica* subsp. *enterica* serovar sofia.

In another embodiment, the bacterium is marked with a selectable marker. Examples of suitable selectable makers include green fluorescent protein (GFP), β-galactosidase, or luciferase, or resistance to an antibiotic such as chloramphenicol, tetracycline, kanamycin, ampicillin, rifampicin or nalidixic acid.

In another embodiment of the present invention, the subject is avian. Preferably, the subject is poultry and more preferably the subject is a chicken.

In another embodiment of the present invention the bacterium colonises a mucosal surface of the subject. Preferably, the bacterium colonises the gut of the subject.

In another embodiment, the one or more biologically active polypeptides is a cytokine, chemokine, hormone, antimicrobial peptide, anti-tumour agent, enzyme, antibody or antigen.

In a preferred embodiment, the cytokine is selected from IL-1β, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-23, IL-24, IL-25, IL-26, IL-32, cMGF, LT, GM-CSF, M-CSF, SCF, IFN-γ, IFN-λ, EPO, G-CSF, LIF, OSM, CNTF, GH, PRL or IFNα/β. Preferably, the cytokine is IL-6.

In another embodiment, the antimicrobial peptide is a colicin, microcin, cecropin, magainin, defensin or bacteriocin such as Piscicolin 126, Divercin V41, Pediocin PA-1, Enterocin P or Divergicin 750, or a synthetic variant of any of these antimicrobial peptides. Preferably, the bacteriocin is Piscicolin 126 or a synthetic variant thereof.

In a preferred embodiment, the Gram negative bacterium is administered orally to the subject.

The present invention also provides a method of identifying a colonising non-pathogenic Gram negative bacterial strain, the method comprising:

i) isolating one or more Gram negative bacterial strain from a subject;

ii) marking the one or more Gram negative bacterial strain;

iii) re-introducing the one or more marked Gram negative bacterial strain into the subject; and iv) determining whether the one or more Gram negative bacterial strain colonises said subject.

Preferably, step (i) involves isolating one or more Gram negative bacterial strain from a site in the subject where delivery of the heterologous polypeptide is eventually required.

In another embodiment, step (i) of this method involves isolating a plurality of bacterial strains.

In another embodiment, step (ii) of this method involves marking a plurality of bacterial strains and step (iii) involves re-introducing a plurality of marked Gram negative bacterial strains into the subject.

In another embodiment, the one or more Gram negative bacterial strain is marked by resistance to one or more antibiotics. Preferably, the one or more antibiotics are rifampicin and/or nalidixic acid.

In yet another embodiment of this method, step (iv) involves isolating a biological sample from the subject and determining whether the sample comprises the one or more marked Gram negative bacterial strain. The sample may be, for example, a tissue or fluid sample, or a swab. Preferably the sample is isolated from a site in the subject where delivery of the heterologous polypeptide is eventually required.

The present invention also provides a colonising non-pathogenic Gram negative bacterial strain isolated by a method of the present invention.

The present invention also provides a method of treating or preventing a disease in a subject, the method comprising administering to the subject a therapeutically effective amount of a colonising non-pathogenic Gram negative bacterium that expresses one or more heterologous biologically active peptides.

The present invention also provides a colonising non-pathogenic Gram negative bacterium that expresses one or more heterologous biologically active peptides, which when administered to a subject, colonises said subject.

In another embodiment of the present invention, the subject is avian. Preferably, the subject is poultry and more preferably the subject is a chicken.

In one embodiment, the bacterium is E. coli. Preferably the E. coli bacterium has the serotype H antigen, H10.

In a preferred embodiment the E. coli strain is selected from CCEC22 as deposited with the National Measurement Institute (formerly AGAL) under accession number NM05/45635, CCEC31 as deposited with the National Measurement Institute (formerly AGAL) under accession number NM05/45636 or CCEC59 as deposited with the National Measurement Institute (formerly AGAL) under accession number NM05/45637 which has been modified to express one or more heterologous biologically active polypeptides.

In another embodiment, the bacterium is a strain of Salmonella. Preferably, the strain is S. enterica subsp. enterica serovar sofia.

In another embodiment, the bacterium is marked with a selectable marker. Examples of suitable selectable makers include green fluorescent protein (GFP), β-galactosidase, or luciferase, or resistance to an antibiotic such as chloramphenicol, tetracycline, kanamycin, ampicillin, rifampicin or nalidixic acid.

In another embodiment the bacterium colonises a mucosal surface of the subject. Preferably the bacterium colonises the gut of the subject.

In another embodiment one or more of the biologically active polypeptides is a cytokine, hormone, enzyme, antimicrobial peptide, anti-tumour agent, enzyme, antibody or antigen.

Preferably the cytokine is selected from IL-1β, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-23, IL-24, IL-25, IL-26, IL-32, cMGF, LT, GM-CSF, M-CSF, SCF, IFN-γ, IFNλ, EPO, G-CSF, LIF, OSM, CNTF, GH, PRL or IFNα/β. In a preferred embodiment the cytokine is IL-6.

In another embodiment one or more of the biologically active polypeptides is an antimicrobial peptide. Preferably the antimicrobial peptide is a colicin, microcin, cecropin, magainin, defensin or bacteriocin such as Piscicolin 126, Divercin V41, Pediocin PA-1, Enterocin P or Divergicin 750, or a synthetic variant of any of these antimicrobial peptides. In a preferred embodiment the bacteriocin is Piscicolin 126 or a synthetic variant thereof.

The present invention also provides a colonising non-pathogenic Gram negative bacterium selected from CCEC22 as deposited with the National Measurement Institute (formerly AGAL) under accession number NM05/45635, CCEC31 as deposited with the National Measurement Institute (formerly AGAL) under accession number NM05/45636 or CCEC59 as deposited with the National Measurement Institute (formerly AGAL) under accession number NM05/45637.

Preferably the Gram negative bacterium is modified to express one or more heterologous biologically active peptides.

The present invention also provides a pharmaceutical formulation that is administered to a subject, comprising a colonising non-pathogenic Gram negative bacterium according to the invention and a pharmaceutically acceptable carrier.

As will be apparent, preferred features and characteristics of one aspect of the invention are applicable to many other aspects of the invention.

BRIEF DESCRIPTION OF THE
ACCOMPANYING DRAWINGS

FIG. 1. Persistence of marked E. coli strains in SPF chickens (Trial 1).

Figure 2:
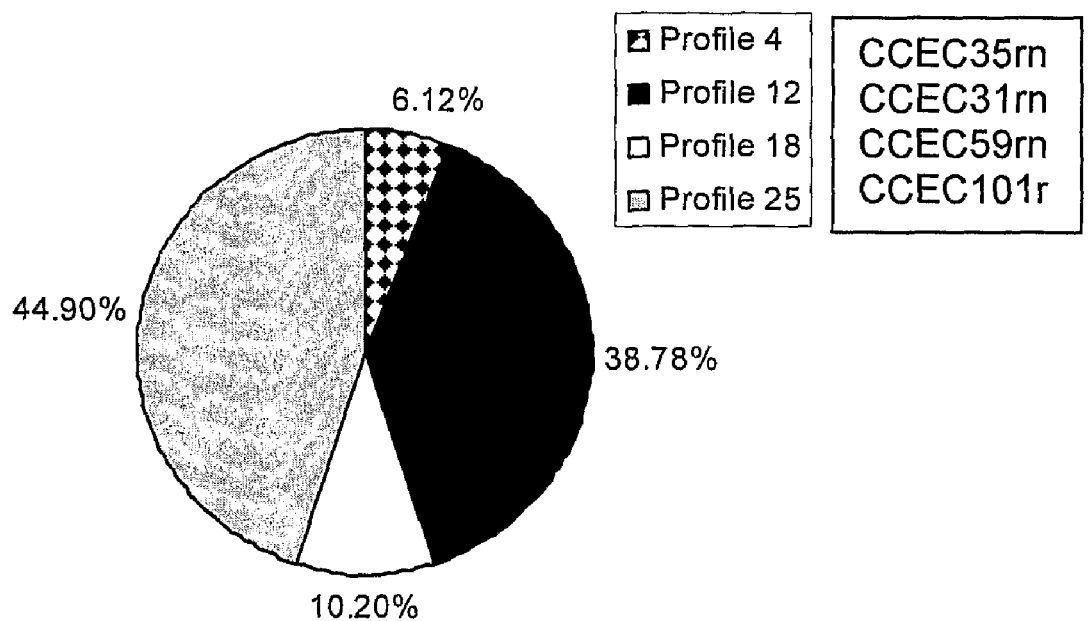

FIG. 2. Percentage of each marked PFGE Xba I digest profile present in chickens 42 days after dosing (Trial 1).

Figure 3:
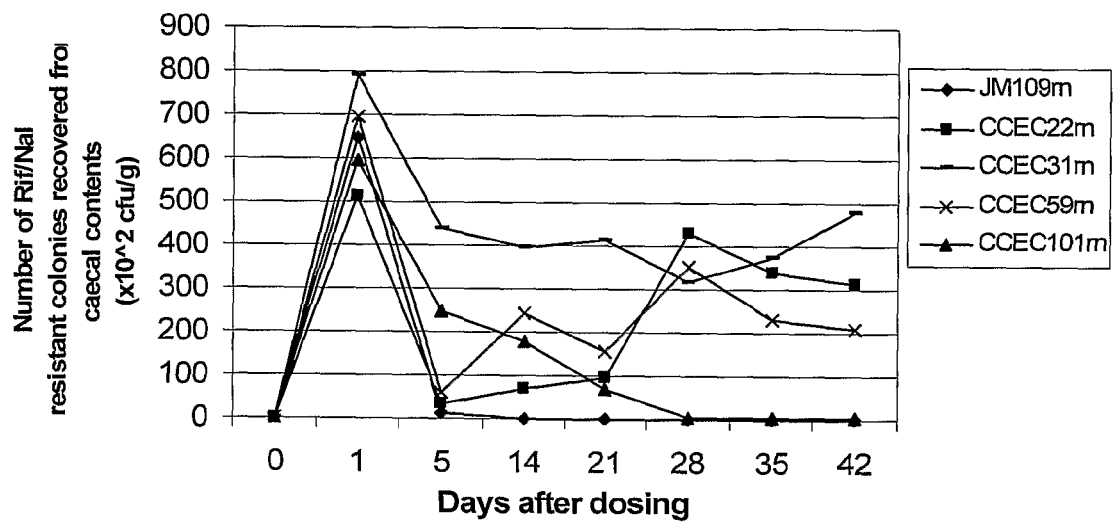

FIG. 3. Persistence of marked *E. coli* strains in commercial chickens. The number of Rif/Nal resistant colonies recovered from caecal contents (Trial 2).

Figure 4:
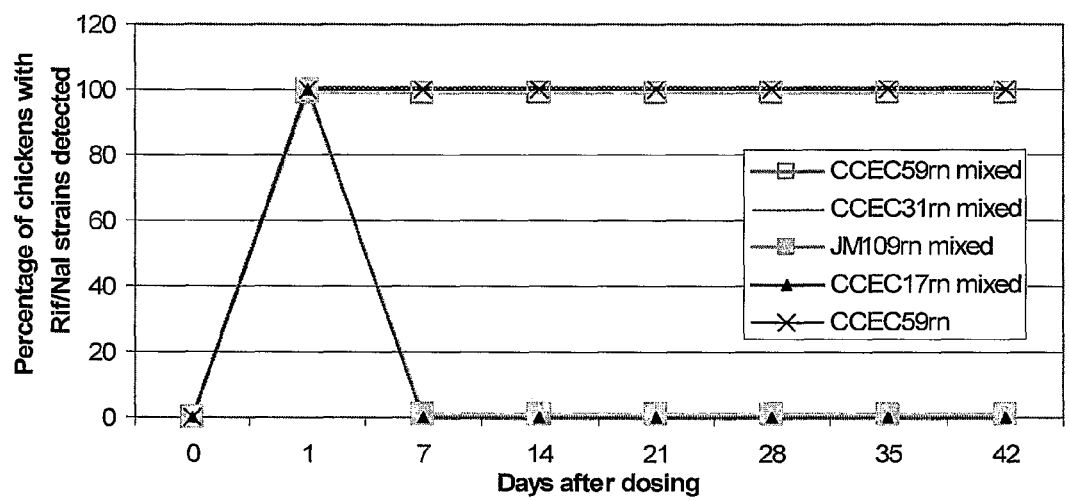

FIG. 4. Persistence of marked *E. coli* strains in commercial chickens. Percentage of chickens with Rif/Nal strains detected (Trial 2).

Figure 5:
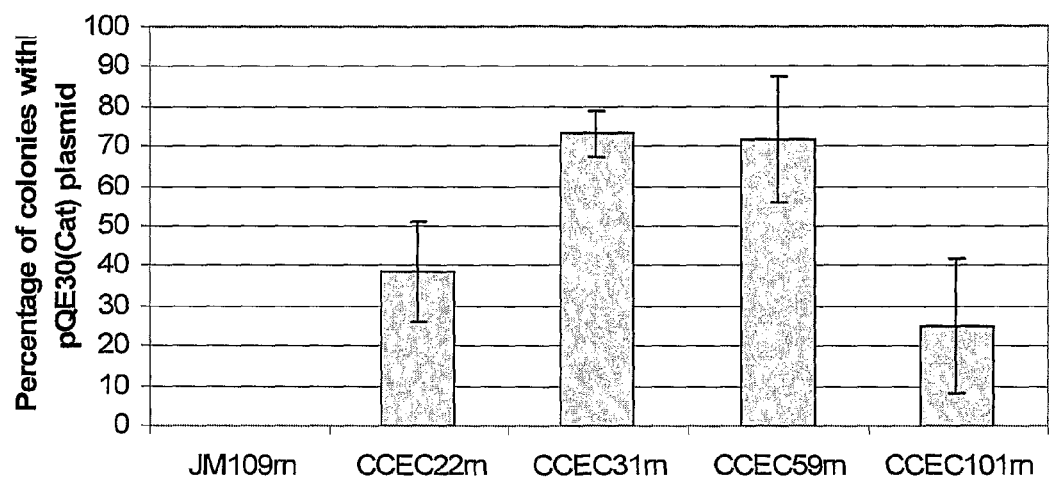

FIG. 5. In vivo plasmid stability of the pQE30(Cat) plasmid at day 28, carried in the marked strains used to dose commercial chickens.

Figure 6:
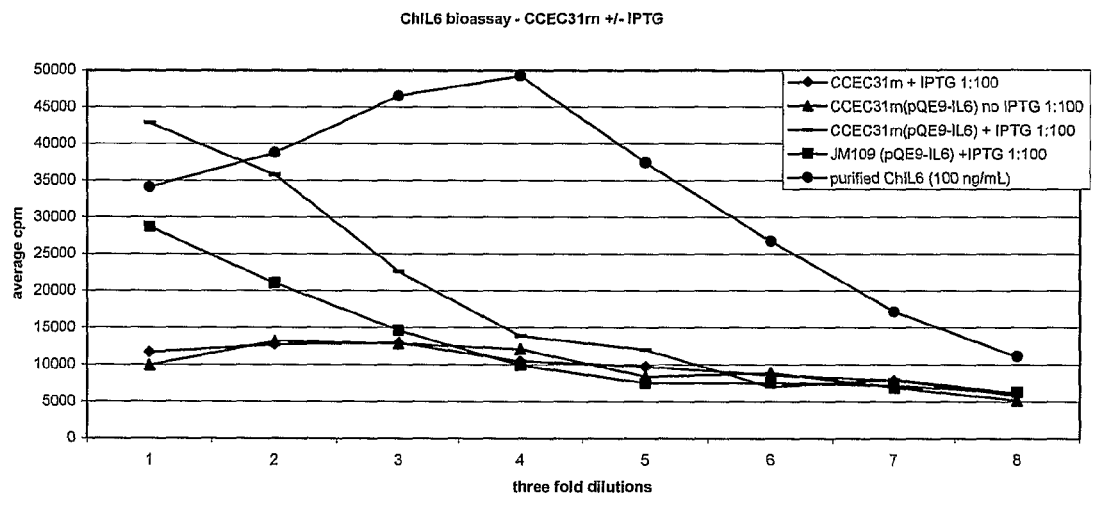

FIG. 6. In vitro biological activity of mature Chicken IL-6 expressed from chicken-derived *E. coli* strain CCEC31rn (+/−1 mM IPTG induction).

Figure 7:
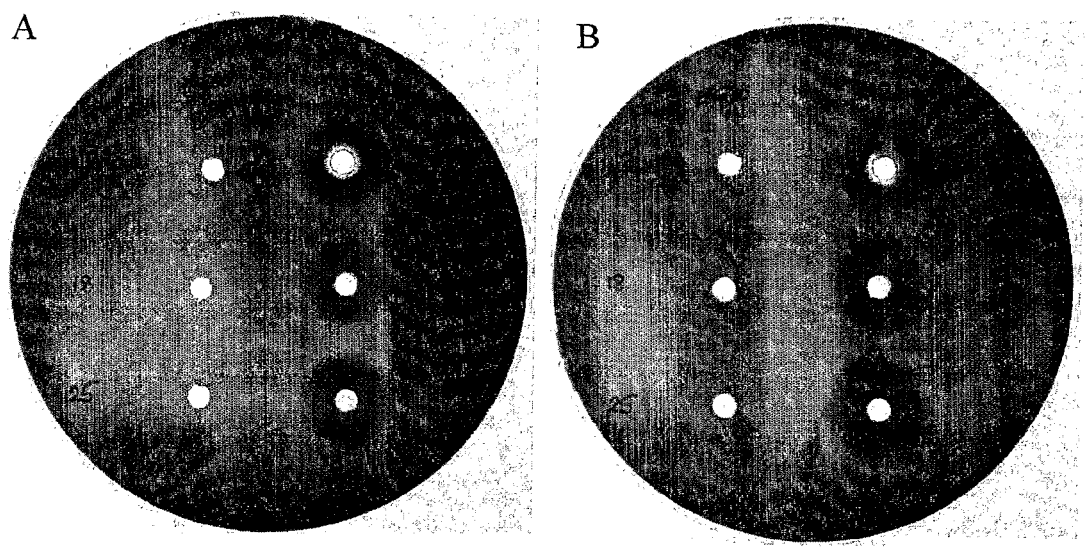

FIG. 7. Plate inhibition assay showing activity of secreted bacteriocin (P126) against *Clostridium perfringens* NE15 (Panel A) and NE18 (Panel B). Chicken-derived *E. coli* vectors carrying the pRM1503 plasmid encoding constitutive expression of the P126 gene were grown overnight, spun down, and 30 μL of filtered supernatant loaded into wells punched into a BHI 5% defibrinated Horse Blood plate pre-flooded with the indicator bacteria. The plate was incubated in anaerobic conditions at 37° C. overnight. The left side of each plate is loaded with supernatant from CCEC strains carrying the vector plasmid pQE30 (no bacteriocin). The right side of each plate is loaded with supernatant from CCEC strains carrying the pRM1503, P126 expression plasmid. Top: CCEC31rn, Middle: CCEC59rn, Bottom: CCEC101rn.

Figure 8:
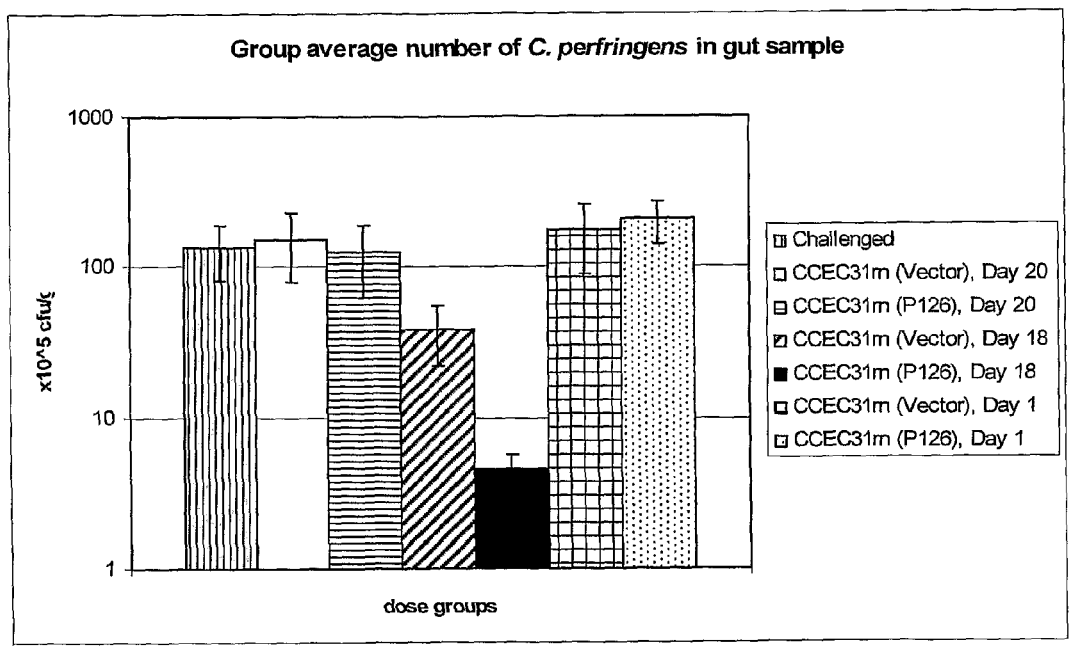

FIG. 8. *C. perfringens* numbers in caecal contents of chickens.

Figure 9:
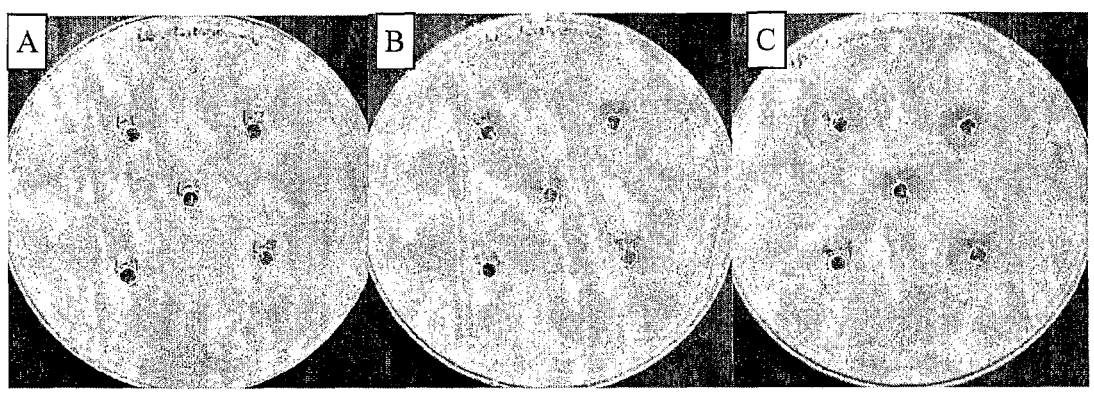

FIG. 9. Bacteriocin activity detected in filtered caecal contents. Filtered caecal contents were centrifuged and neat supernatant plated on *L. innocua*:
A—Controls: CCEC3rn(pQE30), birds 1-5 individual neat supernatants loaded.
B—CCEC31rn(P126), birds 1-5 individual neat supernatants loaded.
C—CCEC3rn(P126), birds 6-10 individual neat supernatant loaded.

Figure 10:
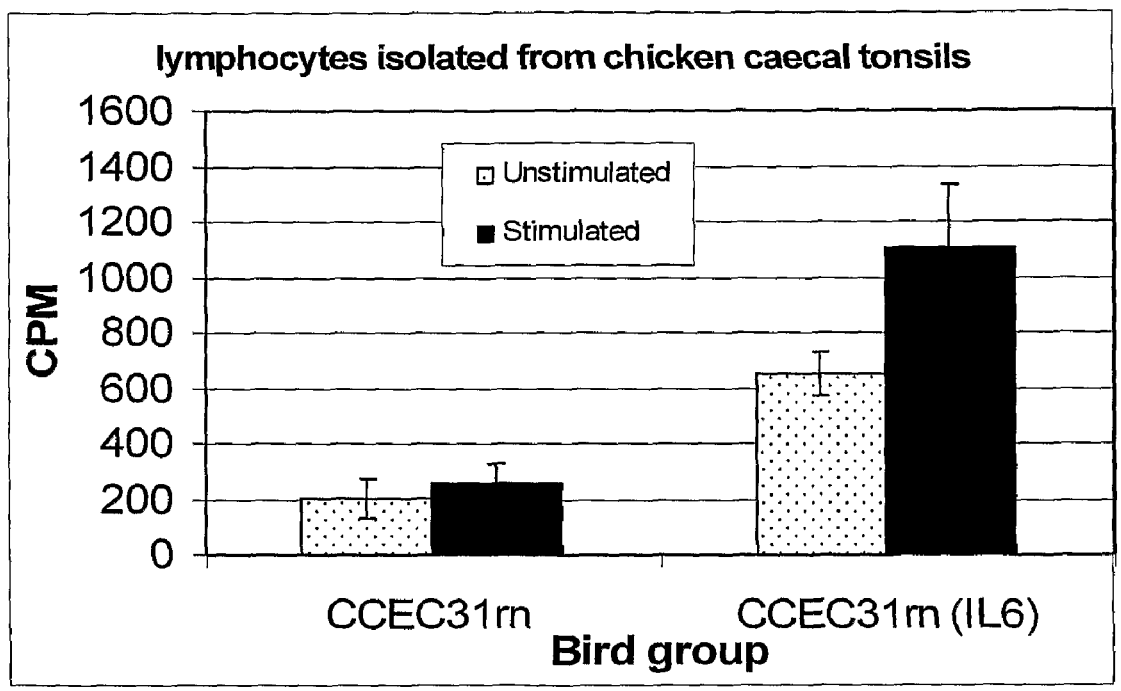

FIG. 10. Proliferation of lymphocytes isolated from chicken caecal tonsils. Difference between the control group (CCEC31rn(pQE30)) and the test group (CCEC31rn(IL-6)) was significant for both unstimulated and stimulated lymphocytes (Mann-Whitney U test, P<0.0001).

Figure 11:
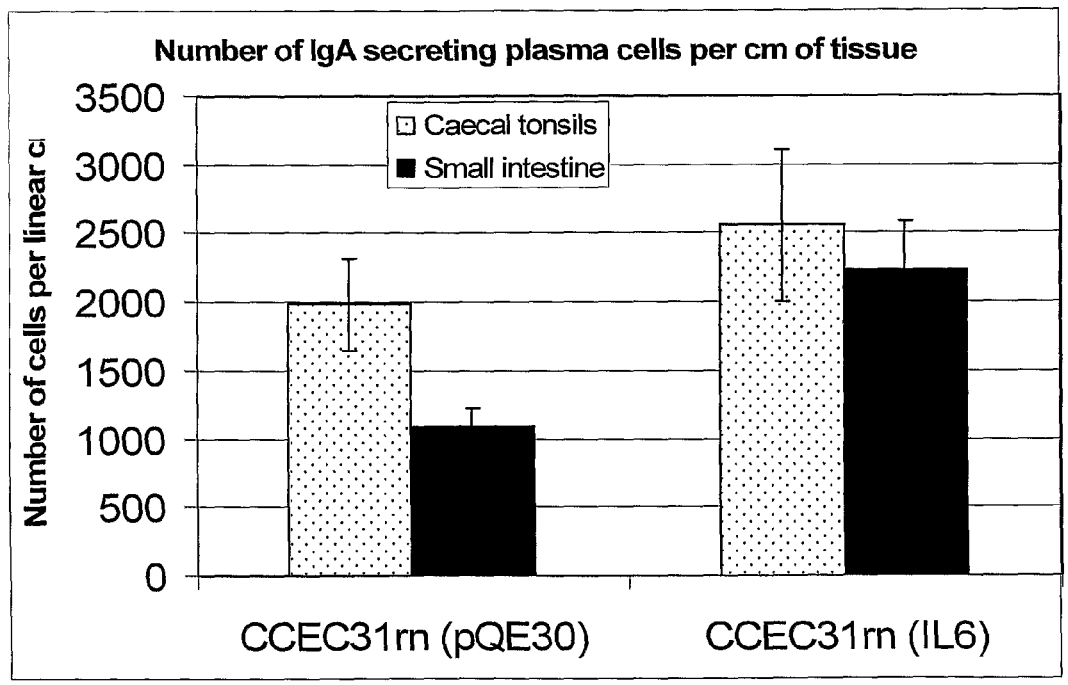

FIG. 11. Number of IgA secreting plasma cells in chickens gut tissues.

Figure 12:
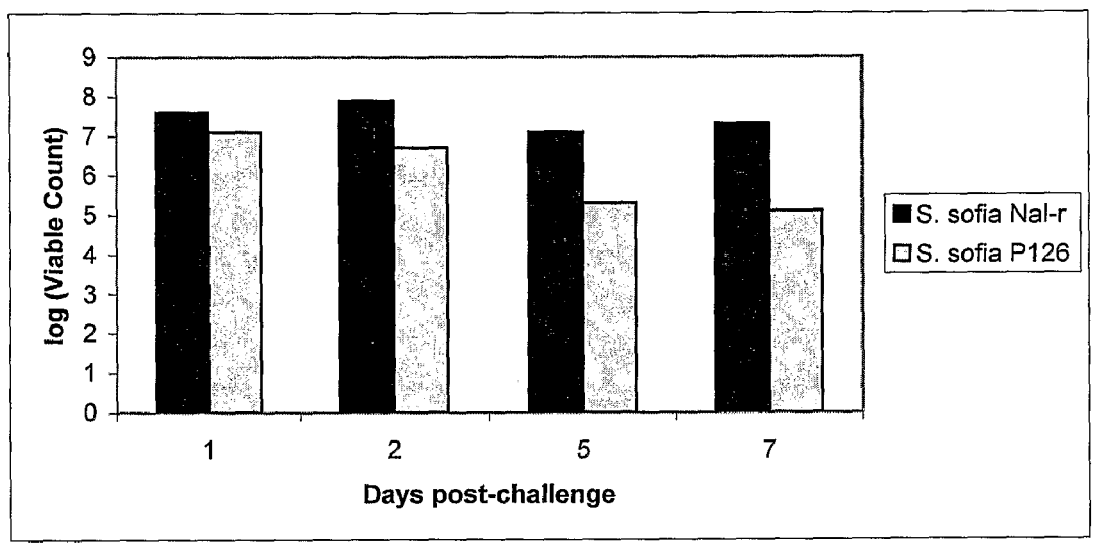

FIG. 12. *Salmonella enterica* subsp. *enterica serovar sofia* populations within the caeca of infected chickens.

Figure 13:
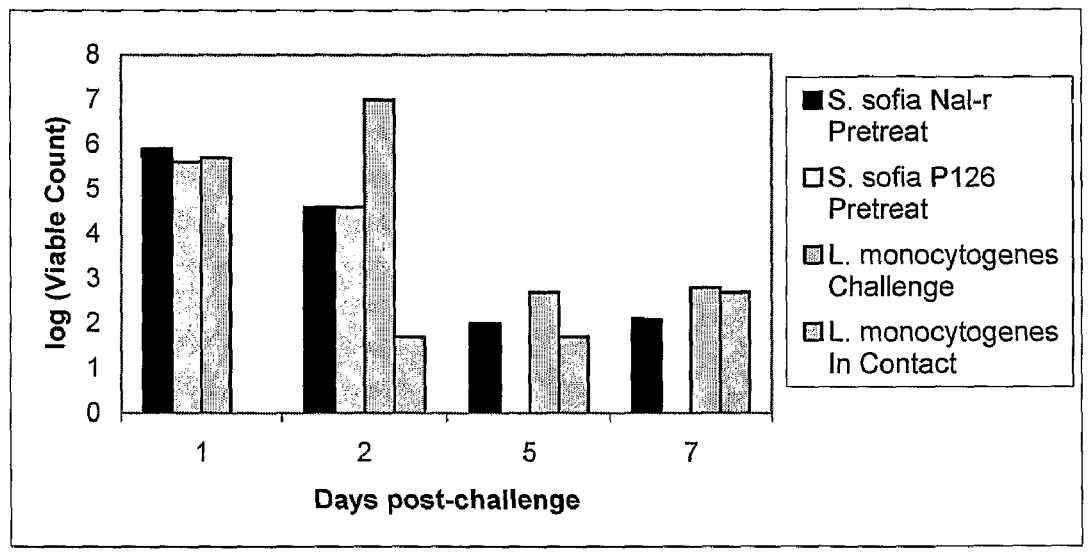

FIG. 13. Proliferation of *L. monocytogenes* in the caecum. Group averages are shown.

DETAILED DESCRIPTION OF THE INVENTION

Micro-organism Deposit Details

The colonising strain of *Escherichia coli* designated CCEC22 was deposited on 12 Aug. 2005 with the National Measurement Institute (formerly AGAL) under accession number NM05/45635.

The colonising strain of *Escherichia coli* designated CCEC31 was deposited on 12 Aug. 2005 with the National Measurement Institute (formerly AGAL) under accession number NM05/45636.

The colonising strain of *Escherichia coli* designated CCEC59 was deposited on 12 Aug. 2005 with the National Measurement Institute (formerly AGAL) under accession number NM05/45637.

These deposits were made under the provisions of the Budapest Treaty on the International Recognition of the Deposit of Microorganisms for the Purpose of Patent Procedure and the Regulations thereunder. This assures maintenance of viable cultures for 30 years from the date of deposit. The organisms will be made available by the National Measurement Institute under the terms of the Budapest Treaty which assures permanent and unrestricted availability of the progeny of the culture to the public upon issuance of the pertinent patent.

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

General Techniques and Definitions

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

For convenience, the term "polypeptide" will hereinafter be used to refer to molecules which are of sufficiently high molecular weight to be called proteins, to products of lesser molecular weight, usually called polypeptides, and to products of even lesser molecular weights normally referred to as peptides.

The term "active polypeptide" is used herein in the broadest possible sense. It refers to any peptide, polypeptide or protein which may be delivered to an animal host for any useful purpose. It includes therapeutic and prophylactic polypeptides and peptides. It could be an antigen, from any pathogenic virus, or from a bacteria, parasite or fungi. In such instances, the active polypeptide may be the complete antigen, the antigenic determinant of the antigen or a segment of the antigen which includes the antigenic determinant. The active polypeptide could also be, by way of non-limiting examples, an antibody, a cytokine, hormone, enzyme, an antimicrobial peptide or a bacteriocin.

"Biological activity" refers to the ability to perform a biological function and, with reference to a polypeptide, implies that the polypeptide adopts a stable conformation ("folded form") which is the same as or closely analogous to its native configuration. When folded correctly or substantially correctly, for example, with formation of proper folded units, α-helices, β-sheets, domains, disulphide bridges, etc., a polypeptide should have the ability to perform its natural function. Generally, the unit of function in a polypeptide is a domain. When used with reference to an antigen, "biological activity" implies that the antigen induces an immune response in a host.

The term "heterologous polypeptide" is well understood in the art and refers to a polypeptide which is not endogenous to a cell, or is a native polypeptide in which the native sequence has been altered, or a native polypeptide whose expression is quantitatively altered as a result of a manipulation of the cell by recombinant DNA techniques. The nucleic acid molecule encoding the polypeptide of interest may originate from any organism capable of producing the polypeptide of interest or may be a completely synthetic gene. The nucleic acid molecule encoding the polypeptide can be added to the cell by, for example, infection, transfection, microinjection, electroporation, microprojection, or the like.

The term "avian" as used herein refers to any species, subspecies or race of organism of the taxonomic class aves, such as, but not limited to, such organisms as chicken, turkey, duck, goose, quail, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, New Hampshire, Rhode Island, Ausstralorp, Minorca, Amrox, California Gray, Italian Partidge-colored), as well as strains of turkeys, pheasants, quails, duck, ostriches and other poultry commonly bred in commercial quantities.

The term "immunogenic composition" covers any composition that elicits an immune response against the targeted pathogen; for instance, after administration or injection into the animal (such as an avian, e.g., chicken), elicits an immune response against the targeted pathogen (e.g., *Clostridium perfringens*).

The term "vaccine" covers any composition that induces a protective immune response against the targeted pathogen or which efficaciously protects against the pathogen; for instance, after administration or injection into the animal (e.g., avian such as chicken or porcine such as pig), elicits a protective immune response against the targeted pathogen or provides efficacious protection against the pathogen (e.g., *C. perfringens*). A subunit of a pathogen, e.g. an antigen or immunogen or epitope isolated from the pathogen, and a subunit composition comprises or consists essentially of one or more antigens, immunogens or epitopes isolated from the pathogen.

The term "antigen" is well understood in the art and refers to the portion of a macromolecule which is specifically recognized by a component of the immune system, e.g., an antibody or a T-cell antigen receptor. The term "antigen" refers to a peptide, a polypeptide, or other macromolecule to which an immune response can be induced in a host. As used herein, the term "antigen" encompasses antigenic epitopes, e.g., fragments of an antigen which are antigenic epitopes. Epitopes are recognized by antibodies in solution, e.g. free from other molecules. Epitopes are recognized by T-cell antigen receptor when the epitope is associated with a class I or class II major histocompatibility complex molecule.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Colonising Gram Negative Bacteria

The bacterium according to the present invention will be a colonising non-pathogenic Gram negative bacterium. Those skilled in the art would understand that Gram negative bacteria include *Salmonella, E. coli, Shigella, Campylobacter, Fusobacterium, Bordetella, Pasteurella, Actinobacillus, Haemophilus* and *Histophilus*. It is envisaged that any strain of a colonising, non-pathogenic Gram negative bacterium may be used in the methods of the present invention.

Preferred examples of colonising, non-pathogenic Gram negative bacterium for use in the methods of the present invention are *Escherichia coli* or a *Salmonella* species such as *S. enterica* subsp. *enterica serovar sofia*.

In a particularly preferred embodiment of the present invention the bacterium is the *E. coli* strain CCEC22 as deposited with the National Measurement Institute (formerly AGAL) under accession number NM05/45635, CCEC31 as deposited with the National Measurement Institute (formerly AGAL) under accession number NM05/45636 or CCEC59 as deposited with the National Measurement Institute (formerly AGAL) under accession number NM05/45637.

In a preferred embodiment of the invention, the *E. coli* strains CCEC22, CCEC31 and/or CCEC59 are used without further modification.

It will be appreciated, however, that further modifications may be made to these strain prior to use. As an example, the *E. coli* strains CCEC22, CCEC31 or CCEC59 may be marked with a selectable marker prior to use. Examples of suitable selectable makers include green fluorescent protein (GFP), β-galactosidase, or luciferase, or resistance to an antibiotic such as chloramphenicol, tetracycline, kanamycin, ampicillin, rifampicin or nalidixic acid.

In one embodiment, the selectable marker is resistance to one or more antibiotics. In one particular example, the *E. coli* strain is marked by resistance to rifampicin (rif) and/or nalidixic acid (nal). This marking may be achieved, for example, by cycling the strain though growth media containing increasing concentrations or rif and/or nal as described herein in Example 3. Antibiotic resistance markers and other markers such as Green Fluorescent Protein can also be introduced to the strains using appropriate plasmids.

Identification of Colonising Gram Negative Bacteria

The present invention also provides a method for identifying a colonising non-pathogenic Gram negative bacterial strain that is useful for delivery of heterologous biologically active polypeptides in vivo.

This method comprises:
  i) isolating one or more Gram negative bacterial strain from a subject;
  ii) marking the one or more Gram negative bacterial strain;
  iii) re-introducing the one or more marked Gram negative bacterial strain into the subject; and
  iv) determining whether the one or more Gram negative bacterial strain colonises said subject.

Preferably, the one or more bacterial strain is isolated from a site in the subject where delivery of the heterologous polypeptide is eventually required.

It will be appreciated that the method of isolation may involve screening large numbers of bacteria in order to identify colonising Gram negative strains that are useful for delivery of heterologous biologically active polypeptides in vivo. For example, a plurality of Gram negative bacterial strains may be isolated from the subject, marked and then reintroduced into the subject.

In one particular example of the method, step (i) involves collecting a range of bacterial strains from a site in the subject where delivery of the heterologous polypeptide is required. The collected bacteria may then be enriched by growth in suitable media before isolating single strains by, for example, streaking onto solid media. Single colonies that resemble Gram negative bacteria, such as those having *E. coli* or *Salmonella* colony morphology, may be isolated and grown on further selective media for confirmation of identification.

Although not necessary, the isolated strains may then be further characterised by phenotypic analysis or by analysis of genetic material. This analysis of genetic material may involve, for example, standard techniques such as pulsed field gel electrophoresis (PFGE) or analysis of the 16S ribosomal RNA gene.

In step (ii) of the method, the isolated strains are then marked with a selectable marker. Any of a range of known selectable markers can be used. In a preferred embodiment the selectable marker is resistance to one or more antibiotics, such as resistance to rifampicin (rif) and/or nalidixic acid (nal). This marking may be achieved, for example, by cycling the strain though growth media containing increasing concentrations or rif and/or nal as described herein in more detail in Example 3.

Step (iii) of the method involves reintroducing the isolated and marked strains into the subject, preferably by oral administration.

Step (iv) of the method involves determining whether or not the marked strains colonise the subject. In a preferred embodiment, step (iv) involves isolating a biological sample (such as a swab) from a site in subject where delivery of the heterologous biologically active polypeptide is desired and determining whether the sample comprises one or more of the marked strains. Preferably, biological samples are isolated from the subject and tested for the presence of marked strains on a number of occasions over a period of time. For example, biological samples may be isolated and tested at various times (such as, for example, every one, two, three, four or five days) over a one to seven week period.

Marked strains that persist in the subject over time particularly over a two week or longer period) following reintroduction to the subject are considered to colonise the subject.

Thus, once a marked colonising strain has been identified it is possible to use that marked strain, or the corresponding isolated unmarked strain, as a vector for delivering biologically active polypeptides to a desired site in a subject.

Biologically Active Polypeptides

The skilled person will appreciate that the methods of the present invention could be used to deliver a range of biologically active polypeptides. Examples of suitable polypeptides include ones which are capable of functioning locally or systemically, e.g., is a polypeptide capable of exerting endocrine activities affecting local or whole-body metabolism.

For example, the biologically active polypeptide may be one which is capable of regulating the immunohemopoietic system. Alternatively, the biologically active polypeptide may be one which is capable of affecting the viability, growth and differentiation of a variety of normal or neoplastic cells in the body. Alternatively, the biologically active polypeptide may be one which is capable of affecting the immune regulation or induction of acute phase inflammatory responses to injury and infection. Alternatively, the biologically active polypeptide may be one which is capable of enhancing or inducing resistance to infection of cells and tissues mediated by chemokines acting on their target cell receptors, or the proliferation of epithelial cells or the promotion of wound healing.

Specific examples of such polypeptides include insulin, growth hormone, prolactin, calcitonin, luteinizing hormone, parathyroid hormone, somatostatin, thyroid-stimulating hormone, vasoactive intestinal polypeptide, a structural group 1 cytokine such as IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-23, IL-24, IL-25, IL-26, IL-32, cMGF, LT, GM-CSF, M-CSF, SCF, IFN-γ, IFN-λ, EPO, G-CSF, LIF, OSM, CNTF, GH, PRL or IFNα/β, a structural group 2 cytokine such as the TNF family of cytokines, e.g., TNFα, TNFβ, CD40, CD27 or FAS ligands, the IL-1 family of cytokines, the fibroblast growth factor family, the platelet-derived growth factors, transforming growth factor β and nerve growth factors, a structural group 3 cytokine, e.g., the epidermal growth factor family of cytokines, the chemokines, the insulin-related cytokines, a structural group 4 cytokine such as the heregulins or neuregulins, e.g., EGF.

Alternatively, the biologically active polypeptide can be a receptor or antagonist for biologically active polypeptides as defined above.

Alternatively, the biologically active polypeptide can be an antigen. If the antigen is from, for example, a bacterial, fungal, parasitic or viral disease agent, the colonising Gram negative bacterial strain can be used to vaccinate a subject against diseases caused by such agents. For example, the colonising Gram negative bacterial strain could be used to deliver an antigen from an avian pathogenic micro-organism. Such micro-organisms include but are not limited to species of *Corynebacteria, Mycoplasma, Listeria, Borrelia, Chlamydia, Clostridia, Coxiella, Eysipelothrix, Flavobacteria, Staphylococcus,* and *Streptococcus.* Examples of fungal and parasitic avian pathogens known to infect poultry are species of *Amoebotaenia, Aproctella, Ascaridia, Aspergillus, Candida, Capillaria, Cryptosporidium, Cyathostroma, Dispharynx, Eimeria, Fimbriaria, Gongylonemia, Heterakis, Histomonas, Oxyspirura, Plasmodium, Raillietina, Strongyloides, Subulura, Syngamus, Tetrameres,* and *Trichostrongylus.* Viruses known to infect poultry include adenoviruses (e.g., hemorrhagic enteritis virus), astroviruses, coronaviruses (e.g., Infectious bronchitis virus), paramyxoviruses (e.g., Newcastle disease virus), picornaviruses (e.g., avian encephalomyelitis virus), pox viruses, retroviruses (e.g., avian leukosis/sarcoma viruses), reoviruses, and rotaviruses. Specific examples include Avian Influenza, Marek's Disease Virus and Chicken Anaemia Virus. Preferred gene products for use as antigens are polypeptides and peptides, including glycoproteins and lipoproteins. Antigen-encoding genes from these prokaryotic and eukaryotic organisms can be cloned and expressed in the colonising Gram negative strain using standard techniques.

In another embodiment of the invention, the biologically active polypeptide is a an antibody, preferably a recombinant antibody. The term "antibody" as used in this invention includes intact molecules as well as fragments thereof, such as Fab, F(ab')2, and Fv which are capable of binding the epitopic determinant. These antibody fragments retain some ability to selectively bind with its antigen or receptor and include:

(1) Fab, the fragment which consists of a complete light chain ($V_L$ and $C_L$) associated with a $V_H$-$C\gamma_1$ fragment of the heavy chain and can be produced by can be produced by digestion of whole antibody with the enzyme papain to yield an intact light chain and a portion of one heavy chain or by introducing DNA encoding the Fab fragment into a non-pathogenic Gram negative bacterium;

(2) Fab', the fragment of an antibody molecule obtained by treating whole antibody with pepsin, followed by reduction, to yield an intact light chain and a portion of the heavy chain (two Fab' fragments are obtained per antibody molecule) or by introducing DNA encoding the Fab' fragment into a non-pathogenic Gram negative bacterium;

(3) (Fab')$_2$, is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; and (6) Single domain antibody, typically a variable heavy domain devoid of a light chain.

Alternatively, the biologically active polypeptide can be an antimicrobial peptide or a synthetic variant thereof. Antimicrobial peptides include cecropins, magainins, and defensins. Cecropins were the first well-characterized family of structurally related antimicrobial peptides and are found in a wide distribution of insects (Boman, 2003). In vertebrates, the magainin family of antimicrobial peptides have been isolated from the glands of the skin and gastrointestinal tract of *Xenopus laevis*, and are thought to form the basis for the defense system of the amphibian mucosal surfaces against infection. (Soravia et al., 1988).

Defensins are antimicrobial peptides found in phagocytic cells isolated from several mammalian species including man and may be characterized by eight invariant residues within the sequence. (Gabay et al., 1989). The mechanism of antimicrobial activity of peptides such as the defensins is via a selective membrane disruption leading to a characteristic broad spectrum of antibiotic activity. (Bowman, 1995). The antimicrobial spectrum of defensins includes gram positive and gram negative bacteria, mycobacteria, many fungi, and some enveloped-viruses.

Antimicrobial peptides of bacterial origin are known as microcins, colicins and bacteriocins (Jack et al., 1995; Ingham et al., 2003). It is known that the sequence, structure and mechanisms of activity of bacteriocins are diverse. The most abundant and thoroughly studied bacteriocins include class I (lantibiotics) and class II (small heat-stable non-lanthionine-containing peptides) bacteriocins (Ennahar et al., 2000). The class II bacteriocins form an important subgroup because of their activities and potential applications. The class IIa bacteriocins include Piscicolin 126, leucocin A and enterocin P amongst others. The class IIa bacteriocins have the common N-terminal motif: YGNGVXaaCXaa(K/N)XaaXaaCXaaV (N/D)(W/K/R)Xaa-(G/A/S)(A/N), where residues with higher variability are represented by Xaa (Bhugaloo-Vial, et al. 1996). In an example demonstrating the antimicrobial properties of bacteriocins, Piscicolin 126, which when injected into mice, was shown to display in vivo antimicrobial activity and significantly reduced the listerial load in the liver and the spleen (Ingham et al., 2003).

Alternatively, the biologically active polypeptide can be an enzyme. The enzyme can be any enzyme having a desired activity. For example, it may be desirable to use the method of the invention to deliver an enzyme that plays a role in improving the digestibility of food or the removal of anti-nutritive compounds. For example, polysaccharide-degrading and fibrolytic enzymes such as xylanases (Liu et al. 2005), glucanases (Cho et al. 2000), cellulases (Liu et al. 2005), amylases, levansucrases, and inulosucrases may be delivered to increase the digestibility of food. Proteinases, peptidases, and lipases may also be delivered in order to increase the nutritive value of ingested foods. Phytases (Vohra and Satyanarayana, 2003; Nahashon et al. 1994) and acid phosphatases (Palacios et al. 2005) may be delivered to reduce the anti-nutritive effects of phytate that is found in plant seeds.

Expression of Biologically Active Polypeptides

The bacterium of the present invention expresses the biologically active polypeptide from nucleic acid contained within it. The nucleic acid may comprise one or more nucleic acid constructs in which nucleic acid encoding the biologically active polypeptide are under the control of appropriate regulatory sequences for expression in the bacterium.

Suitable vectors, such as that described by Ingham et al. (Ingham et al., 2005), comprising nucleic acid for introduction into bacteria can be chosen or constructed containing appropriate regulatory sequences, including promoter sequences, terminator fragments, enhancer sequences, marker genes and other sequences as appropriate. Vectors may be plasmids, viral, e.g., phage or phagemid, as appropriate. For further details see, for example, Molecular Cloning. a Laboratory Manual: 2nd edition, Sambrook et al., 1989, Cold Spring Harbor Laboratory Press. Many known techniques and protocols for manipulation of nucleic acid, for example, in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

The coding sequences for the biologically active polypeptide may be contained in an operon, i.e., a nucleic acid construct for multi-cistronic expression. In an operon, transcription from the promoter results in an mRNA which comprises more than one coding sequence, each with its own suitably positioned ribosome binding site upstream. Thus, more than one polypeptide can be translated from a single mRNA. Use of an operon therefore enables expression of more than one biologically active polypeptide by the bacterium of the present invention.

Alternatively, the coding sequences for two separate biologically active polypeptides can be part of the same nucleic acid vector, or separate vectors, where they are individually under the regulatory control of separate promoters. The promoters may be the same or different.

A promoter employed in accordance with the present invention is preferably expressed constitutively in the bacterium. Use of a constitutive promoter avoids the need to supply an inducer or other regulatory signal for expression to take place. Preferably, the promoter directs expression at a level at which the bacterial host cell remains viable, i.e., retains some metabolic activity, even if growth is not maintained. Advantageously, such expression may be at a low level. For example, where the expression product accumulates intracellularly, the level of expression may lead to accumulation of the expression product at less than about 10% of cellular protein, preferably about or less than about 5%, for example, about 1-3%. The promoter may be homologous to the bacterium employed, i.e., one found in that bacterium in nature. For example, a promoter that is functional in *E. coli* may be used. The promoter could be, by way of a non-limiting example, the T5 phage promoter which is functional in *E. coli*.

As will be appreciated by those skilled in the art, the biologically active polypeptide may include a signal sequence that provides for secretion of the expressed protein in the Gram negative bacteria. The signal sequence preferably encodes a signal peptide which directs the secretion of the protein from the cell via a bacterial secretion mechanism. The protein can be secreted into the growth media, into the periplasmic space located between the inner and outer membrane of the cell, or to the cell surface. The expressed protein may also be accumulated within inclusion bodies within a bacterial cell wall.

An example of a bacterial secretion mechanism that can be used in the present invention is the type I secretion mechanism of *E. coli* that utilises the α-haemolysin (HlyA) transporter (Mergulhao, 2005). Recombinant polypeptides targeted for secretion contain a signal sequence comprising the C-terminal region of HlyA. Alternative secretion mechanisms include the SecB-dependent pathway, the signal recognition pathway (SRP) and the twin-arginine translocation pathway (Mergulhao, 2005). Other non-limiting examples of suitable bacterial secretion signals include PelB, OmpA, PhoA and MalE (Choi 2004).

Methods for expressing recombinant proteins at the cell surface are well known in the art. By way of example, a vector for expressing recombinant lipoproteins on the bacterial cell surface is described in Cullen et al. (2003), and the Autodisplay system that exploits the natural secretion mechanism of AIDA-I transporter protein is described by Jose (2006).

Immunogenic or Vaccine Compositions The immunogenic compositions (or vaccines) of the invention comprise a colonising non-pathogenic Gram negative bacterium according to the invention which expresses one or more heterologous antigens and/or immunoregulatory proteins. For example, the one or more antigens may be an antigenic polypeptide from a bacterial pathogen such as *Clostridium perfringens*. The one or more immunoregulatory proteins of the immunogenic composition may function as an adjuvant. Examples of polypeptides that can function as adjuvants include cytokines such as IL-6 and IL-2. The immunogenic composition may further comprise a pharmaceutically or veterinarily acceptable carrier. In another embodiment, the immunoregulatory protein is delivered alone.

As is known to one skilled in the art, the immunogenic composition or vaccine may be combined with one or more immunogens, antigens or epitopes selected from other microorganisms or viruses in a live or inactivated form.

Pharmaceutical Formulations

The formulations of the invention include bulk drug formulations useful in the manufacture of pharmaceutical formulations. Such formulations comprise a prophylactically or therapeutically effective amount of a colonising Gram negative bacterium and a pharmaceutically acceptable carrier. A pharmaceutically acceptable carrier includes a veterinarily acceptable carrier. Preferably, formulations of the invention comprise therapeutically effective amount of one or more colonising Gram negative bacteria of the invention and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like.

Generally, the ingredients of formulations of the invention are supplied either separately or mixed together in unit dosage form, for example, as a dry lyophilized powder or water free concentrate in a hermetically sealed container such as an ampoule or sachet indicating the quantity of active agent.

To deliver the bacteria to the gastrointestinal tract or to the nasal passages, the preferred mode of administration is by oral ingestion or nasal aerosol, or by feeding (alone or incorporated into the subject's feed or food or water supply). In this regard, it should be noted that probiotic bacteria, such as *Lactobacillus acidophilus*, are sold as gel capsules containing a lyophilized mixture of bacterial cells and a solid support such as mannitol. When the gel capsule is ingested with liquid, the lyophilized cells are re-hydrated and become viable bacteria. Thus, in a similar fashion, Gram negative bacterial cells of the present invention can be supplied as a powdered, lyophilized preparation in a gel capsule, or in bulk for sprinkling into food or beverages. The re-hydrated, viable bacterial cells will then populate and/or colonize sites throughout the upper and lower gastrointestinal system.

For topical applications, the bacteria may be formulated as an ointment or cream to be spread on the affected skin surface. Ointment or cream formulations are also suitable for rectal or vaginal delivery, along with other standard formulations, such as suppositories. The appropriate formulations for topical, vaginal or rectal administration are well known to medicinal chemists.

The present invention will be of particular utility for mucosal administration to treat a variety of bacterial infections or bacterially related undesirable conditions.

The invention is hereinafter described by way of the following non-limiting Examples and with reference to the accompanying figures.

EXAMPLES

Example 1

Isolation of *E. coli* strains from chickens

A range of bacterial species were collected from commercial chickens by swabbing the cloaca and by collecting the caecal contents of birds. The collected bacteria were enriched by overnight growth of each swab in 2 mL of MacConkey broth (MacConkey, 1905) at 37° C., before streaking a loop of enriched culture onto MacConkey agar plates that were incubated at 37° C. overnight. Single colonies that resembled typical *E. coli* colony morphology were streaked onto Eosin Methylene-Blue Lactose Sucrose (EMB) agar (Holt-Harris and Teague, 1916) plates, grown at 37° C. overnight and then frozen stocks were prepared in 80% glycerol. Presumptive *E. coli* strains were designated CCEC1 to 101, and termed CSIRO Chicken *E. coli* (CCEC) strains. Collected CCEC strains were grown on further selective media agar (Xylose Lysine Deoxycholate (XLD) agar (Taylor, 1965) and agar for the identification of *Salmonella* according to Onoz (Onoz and Hoffinan, 1978) for confirmative identification of *E. coli* according to the characteristic colony morphology observed on plates. Any of the CCEC isolates that were not identified as *E. coli* on the selective agar plates were not used for further analysis.

To confirm the initial identification, a portion of the 16S ribosomal RNA (rRNA) gene from CCEC isolates was amplified by PCR. The PCR primers amplified a variable region of the 16S rRNA gene which allowed discrimination amongst a wide variety of bacterial species. When the PCR product was purified, sequenced and aligned in a blastn search, the 630 bp product of all selected CCEC isolates had the closest sequence identity to the *E. coli* 16S rRNA sequence. Hence, CCEC isolates collected from chicken caecal contents and cloacal swabs were identified as *E. coli* by gene sequence, and growth and colony morphology on indicator media.

Example 2

Subtyping of *E. coli* Isolates by Pulse-field Electrophoresis

*E. coli* strains (CCEC isolates) were further analysed using a pulsed-field gel electrophoresis (PFGE) typing technique.

After analysis of all isolates, 25 different XbaI-digested DNA profiles were found within the collection.

Example 3

Generation of Antibiotic Resistant E. coli Strains

Representative strains from the different PFGE sub-types were repeatedly cycled through broth containing increasing concentrations of the antibiotics rifampicin or nalidixic acid in order to isolate strain variants with selectable levels of resistance to these antibiotics. The rifampicin resistant mutants were subsequently subcultured through increasing levels of nalidixic acid to select strains resistant to both antibiotics. From the isolates representative of the different PFGE sub-types we isolated derivatives that were resistant to rifampicin (rif), another set of derivatives resistant to nalidixic acid (nal), and a third set resistant to both antibiotics (rif/nal).

Example 4

Identification of E. coli Strains that Persist in the Gastro-intestinal Tract of Specific Pathogen Free (SPF) Chickens (Trial 1)

14 SPF chickens were orally dosed with 1 mL of a mixed E. coli culture containing each of the doubly marked PFGE sub-type isolates. Five in-contact birds were not dosed directly with the E. coli culture. Cloacal swabs were taken from the birds every second day to check for presence of the marked strains. Swabs were taken up to day 42 to study how long marked strains persisted in the chickens (FIG. 1). Before dosing with the mixed E. coli culture no doubly resistant (rif/nal) bacterial isolates were detected. After dosing marked strains could be readily isolated from all birds on every sampling point for the 42 day duration of the trial. Doubly resistant E. coli could be isolated form all the in-contact birds one day after dosing the other chickens, indicating rapid spread to co-housed birds. When doubly marked strains were isolated from the caecal contents of dosed chickens only 4 PFGE sub-type profiles were recovered (FIG. 2), indicating that these strains persisted whereas all other strains were undetectable at the level of analysis that was performed.

Example 5

Serotyping of Persistent E. coli Strains

Although the E. coli strains were originally isolated from healthy chickens and the subsequent dosing of chickens has not indicated any adverse health implications, we next confirmed that the strains are harmless, non-pathogenic members of the commensal flora by determining their serotypes and looking for the presence of known virulence factors. The strains CCEC31rn, CCEC59rn and CCEC101rn were typed by the National E. coli Laboratory (Microbiological Diagnostic Unit, Department of Microbiology, University of Melbourne, Australia) for confirmation of the identification of the micro-organism, serotyping of the O and H antigens, and the production of any common virulence factors from these strains. All 3 samples were identified as E. coli, and all have the serotype H antigen, H10. Strain CCEC31rn was shown to express an α-haemolysin, and carried the O antigen (Ont). Strains CCEC59rn and CCEC101rn were both typed as E. coli OR:H10 and were not haemolytic. Neither Ont:H10 or OR:H10 E. coli have been recorded in the literature to be responsible for any major disease outbreaks or illnesses in humans or animals. All 3 strains were not verocytotoxic, did not produce Shiga toxins or produce any Cytotoxic Necrotizing Factors.

Example 6

Persistence of E. coli Sub-types in Commercial Chickens (Trial 2)

This trial was essentially the same as that outlined in Example 5 except that commercial broiler chickens were used. A summary of the trial results is presented in FIGS. 3 and 4. In this trial strains CCEC31rn, 59rn, and 101rn were recovered as in the first trial but CCEC35rn, which made up a small percentage of the population recovered in Trial 1, was not recovered in Trial 2. However, CCEC22rn was recovered in good numbers from the commercial birds but was not seen in Trial 1. A laboratory strain of E. coli, JM109, was rapidly lost from the chickens and could not be recovered after day 5.

Example 7

Transformability, Plasmid Stability and Recombinant Protein Expression from the Persistent E. coli Strains A number of E. coli isolates were shown to persist in the gut of both SPF and commercial chickens and hence were good candidates for use as live vectors. A second requirement for use as vectors is that it must be possible to genetically manipulate the strains to express the recombinant proteins that are to be delivered. We therefore tested the ability of the persistent strains to be transformed with a cloning vector plasmid and express a model protein, Green Fluorescent Protein (GFP). E. coli strains CCEC22rn, 31rn, 59rn, and 101rn were all readily transformable with the expression cloning vector pQE30 using standard E. coli electro-transformation techniques. When the pTracer-CMV2 plasmid carrying the Green Fluorescent Protein (GFP) was introduced into the strains, CCEC31rn, 59rn, and 101rn, all 3 strains displayed a bright green fluorescent phenotype under UV light. Similarly, when the transformed cells were grown in liquid culture and observed using a fluorescence microscope, all cells expressed the GFP gene. Therefore, the persistent E. coli strains can efficiently express recombinant protein.

The in vivo stability of the plasmids within the persistent strains was also measured. The plasmid stability of a standard expression cloning plasmid, pQE30(Cat) carried by each of the marked strains inoculated into commercial chickens was assessed 28 days after dosing. Colonies isolated from birds dosed with strains CCEC31rn and CCEC59rn had a high plasmid stability with 73±6% and 71±16% of colonies retaining expression of the plasmid encoded antibiotic resistance. Colonies isolated from birds dosed with strains CCEC22rn and CCEC101rn had lower plasmid stability, at 38±13% and 25±17% respectively as shown in FIG. 5.

Example 8

Detection of IL-6 Protein Expressed from Chicken Derived E. coli Vectors

The plasmid pQE9-IL-6 contains the mature chicken Interleukin-6 (IL-6) gene, and was introduced into the chicken derived E. coli vectors. Recombinant chicken IL-6 was expressed from the chicken-derived E. coli vectors as evidenced by an induced protein band with a molecular weight of approximately 27 KDa. The in vitro biological activity of cell supernatants were measured in an IL-6 induced cellular proliferation bioassay (FIG. 6). Supernatants from CCEC31rn (pQE9-IL-6) induced with IPTG showed significant biological activity whereas the same strain uninduced or without the expression plasmid showed no biological activity in the IL-6 bioassay. CCEC31rn(pQE9-IL-6) produced a higher level of IL-6 activity than the commonly used laboratory strain JM109 carrying the expression plasmid. The persistent *E. coli* strain CCEC3 rn is clearly able to produce recombinant IL-6, a cytokine with potential therapeutic uses.

Example 9

Anti-bacterial Activity of Piscicolin 126 (P126) Secreted by the *E. coli* Vectors Plasmids constitutively expressing the bacteriocin P126 in the *E. coli* vector strains CCEC31rn, CCEC59rn and CCEC101rn were tested for secretion of in vitro bacteriocin activity by plate inhibition assay. *Listeria innocua* and *Clostridium perfringens* (Strain NE15 and NE18, CSIRO collection) were grown in the laboratory and plated as test organisms in bacteriocin plate inhibition assays. Secreted P126 in the supernatants of chicken-derived *E. coli* strains have inhibited the growth of both *L. innocua*, and the *C. perfringens* NE strains that were tested in the assay (FIG. 7).

Example 10

Delivery of Therapeutic Proteins to the Gut of Chickens

One of the persistent *E. coli* strains (CCEC31rn) was used to demonstrate the efficacy of the live vectoring approach in delivering therapeutic recombinant proteins to the gut of chickens. Plasmids carrying the genes encoding the proteins to be delivered were introduced into this strain as defined below:

| Strain (Plasmid) | Designation | Protein encoded | Other comments |
|---|---|---|---|
| CCEC31rn (pRM1503) | CCEC31rn (P126) | Piscicolin 126 (P126) | $Rif200^R Nal35^R Chl35^R$ |
| CCEC31rn (pQE9-IL6) | CCEC31rn (IL-6) | Mature Chicken IL-6 | $Rif200^R Nal35^R$ IL-6 inducible |
| CCEC31rn (pQE30) Cat | CCEC31rn (pQE30) | — | $Rif200^R Nal35^R Chl35^R$ Strain control (base plasmid) |

*E. coli* strains carrying plasmids as described above were grown to mid log phase and then each chicken received a 1 mL oral dose of the neat culture. Three different times for *E. coli* dosing were tested, day 1, day 18, and day 20 post-hatch. On days 21 and 22 post hatch, birds were experimentally challenged with *C. perfringens* by oral inoculation of a 1 mL culture of *C. perfringens* chicken isolate NE15 (capable of producing a high level of disease). The feed was withdrawn from the pen for 24 hrs between the 2 challenge doses, and when returned, was inoculated with 20 mL of *C. perfringens* culture per pen. The birds were autopsied three days after the second challenge; the intestines of each bird were examined for focal lesions of necrosis or ulceration to assess the level of necrotic enteritis.

Example 11

Delivery of P126

Chickens inoculated with CCEC31rn(P126) on day 18 were completely protected from the *C. perfringens* challenge (ie. no lesions were seen in any chickens in this group) compared to the relevant control group and the challenge control group. Chickens dosed with this strain and plasmid on other days (day 1 or day 20) did not show any protection (reduction of lesion score) from challenge with *C. perfringens* compared to their relevant dose control group or the challenge control group.

Following autopsy, *C. perfringens* numbers in the caecal contents of the chickens dosed were determined by plating dilutions on BHI horse blood agar (incubated anaerobically at 37° C.). Results shown in FIG. 8 demonstrate that *C. perfringens* numbers collected from chickens that were dosed with CCEC31rn(P126) on day 18 were significantly reduced compared to the other groups, including the relevant vector control group (*E. coli* (vector), day 18). This group was the same group of chickens that previously showed protection (reduced number of lesions) after challenge with *C. perfringens*. Therefore, appropriately timed delivery of P126 in this *E. coli* vector has a prophylactic action; stopping the development of necrotic enteritis in chickens.

Example 12

Detection of Anti-microbial Activity in Chicken Caecal Contents

In a separate trial, commercial broiler chickens were dosed with CCEC31rn(P126) and relevant vector controls and were autopsied 3 days post challenge. The presence of active P126 protein in the gut of chickens was investigated by sampling the caecal contents, resuspending in PBS, centrifuging, and then filtering the supernatant through a 0.22 μm filter. 30 μL of supernatant was loaded into the wells of an inhibition plate seeded with *L. innocua* or *C. perfringens*. The plate was incubated at 37° C. overnight, and zones of inhibition assessed (FIG. 9).

Bacteriocin activity, as demonstrated by the zones of bacterial killing, was clearly recovered from the caeca of all birds dosed with CCEC31rn(P126). No antibacterial activity was detected in the caeca of control birds dosed with CCEC31rn (pQE30). It is clear that the persistent strains of *E. coli* isolated from chickens are capable of delivering the potentially therapeutic protein Piscicolin 126 to the gut of chickens. When delivered at an appropriate time it can completely stop the development of the serious chicken disease, necrotic enteritis.

Example 13

Delivery of IL-6 to Chickens

Mature chicken IL-6 was delivered to chickens using the *E. coli* vector CCEC3rn. Chickens were dosed with 1 mL of CCEC3rn(IL-6) or CCEC31rn(pQE30) induced culture on days 1 and 18, and tissue samples were collected from the gut to assess the biological effects of live vectored delivery of IL-6.

IL-6 is reported to stimulate B cell differentiation and proliferation in vitro and in vivo. In the presence of IL-6, B cells are able to differentiate into IgA producing plasma cells, and IgA is secreted onto mucosal surfaces to provide protection to the chicken from pathogens entering the body by mucosa membrane borders. Hence, IL-6 has a major role in mucosal immunity, and the correct delivery of IL-6 to the gastro-intestinal tract of chickens can be assessed by observing an increased proliferation of B cells (lymphocytes) in the intestinal lining; an increased number of plasma cells; and an increased production of IgA and secretion onto the mucosal surface.

Example 14

Lymphocyte Proliferation in Chickens Dosed with CCEC3rn(IL-6)

At autopsy, lymphocytes were extracted from the caecal tonsils and the intestinal lining of the chickens. After counting, equal numbers of lymphocytes from both samples were used in a proliferation assay to assess the ability of these lymphocytes to proliferate, measured using a radioactive label incorporated into the multiplying cells.

Lymphocytes isolated from the caecal tonsils of chickens dosed with IL-6 had a higher proliferation potential than lymphocytes from the control chickens inoculated with CCEC31rn(pQE30) both with and without stimulation with a mitogen, ConA (FIG. 10). Cells that can proliferate without stimulation are presumed to have been activated previously, and are highly activated for defense. The results were statistically significant in a Mann-Whitney U test. It is clear that lymphocytes isolated from birds dosed with CCEC31rn(IL-6) have a higher potential to proliferate than lymphocytes isolated from birds that were dosed with the $E.$ $coli$ vector carrying just the base plasmid. This demonstrates that the IL-6 is being effectively delivered to the gastro-intestinal tract of the chicken via the $E.$ $coli$ vector, and the delivered IL-6 product is having an effect on the B lymphocyte cells of the chicken.

Example 15

Number of IgA Secreting Cells in the Intestinal Lining and Caecal Tonsils of Dosed Chickens Sections of the caecal tonsils and intestinal lining were stained for IgA and the number of IgA secreting plasma cells per linear cm of tissue in each sample was counted. In samples collected from the intestinal lining (FIG. 11), birds dosed with the $E.$ $coli$ vector strain expressing IL-6 had higher numbers of IgA secreting cells per linear cm of tissue than birds in the group that were dosed with the vector strain carrying the base plasmid. The difference between these 2 groups were significant (P=0.0286) when tested in a Mann-Whitney U test. Average counts between the 2 chicken groups collected from the caecal tonsils of these birds were not statistically different, as expected from cells isolated from tissues that are not directly involved in mucosal immunity.

Example 16

Delivery of Piscicolin 126 to Chickens using $S.$ $sofia$

The $S.$ $sofia$ expressing P126 was tested in the chicken listeriosis model. Four groups, each of ten SPF chickens, were housed in two bubble isolators (groups 1 and 2 in one isolator and 3 and 4 in the other). The treatment groups were as follows:
1. $S.$ $sofia$ Nalr and $L.$ $monocytogenes$ challenge
2. $S.$ $sofia$ Nalr (P126) and $L.$ $monocytogenes$ challenge
3. $L.$ $monocytogenes$ challenge only
4. Unchallenged Groups 1 and 2 received approximately $10^9$ cfu of the appropriate $S.$ $sofia$ strain at 1 day of age. On day 2 groups 1, 2, and 3 received $2\times10^8$ cfu of $L.$ $monocytogenes$. The general health of the birds was observed throughout the trial and 2 birds were killed and bacteria enumerated on days 1, 2, 5, and 7 post-challenge.

The results showed that the populations of $S.$ $sofia$ were maintained at a high level throughout the trial (FIG. 12) and $L.$ $monocytogenes$ could not be recovered after day 2 from the group pre-treated with the $S.$ $sofia$ expressing P126 but was found in all the other groups, including the in-contact control birds (FIG. 13).

Conclusion

The results demonstrate that a small percentage of $E.$ $coli$ isolates recovered from healthy chickens have the ability to persist. The methods outlined define how such isolates can be identified and tested. A number of persistent strains have been identified and shown subsequently to have other characteristics required to make a useful live delivery vector; they are transformable with plasmid DNA, can maintain plasmid vectors in in vivo conditions, and can express a model recombinant protein.

It is clear that the persistent strains of $E.$ $coli$ isolated from chickens are capable of delivering the potentially therapeutic protein Piscicolin 126 to the gut of chickens. When delivered at an appropriate time it can completely stop the development of the serious chicken disease, necrotic enteritis.

IL-6 delivery via the $E.$ $coli$ vector CCEC3rn has increased differentiation of B cells in the intestinal lining of the chicken gastro-intestinal tract into plasma cells that are able to secrete IgA onto mucosal surfaces for mucosal defense. The delivery of IL-6 to the gastro-intestinal tract of chickens by the selected bacterial vector has been successful, and has stimulated B cells of the immune system to proliferate and differentiate in order to prepare the chicken immune system for pathogen invasion and immune counterattack.

Piscicolin 126 was also delivered to chickens using $S.$ $sofia$. The results demonstrated that $S.$ $sofia$ can be maintained in chickens, and that the bacterially delivered Piscicolin 126 was active against $Listeria$ $monocytogenes$ in vivo.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Bermudez-Humaran, L G (2003) Infect Immun. 71: 1887-1896
Bhugaloo-Vial, P et al., (1996) Appl Environ Microbiol. 62: 4410-4416
Boman, H G (1995) Annu Rev Immunol. 13: 61-92
Boman, H G (2003) J Intern Med. 254: 197-215

Cho, J S et al. (2000) Curr Microbiol. 40: 257-263
Choi, J H and Lee, S Y (2004) Appl Microbiol Biotechnol. 64:625-635
Cowen, B S et al. (1987) Avian Dis. 31: 904-906
Craven, S E et al. (1999) Avian Dis. 43: 484-490
Cullen, P A et al. (2003) Plasmid. 49: 18-29
Devriese, L A et al. (1993) J Appl Bacteriol. 75: 55-57
Ennahar, S et al. (2000) FEMS Microbiol Rev. 24: 85-106
Gabay, J E et al (1989) Proc Natl Acad Sci USA. 86: 10183
Garmory, H S et al., (2003) J Drug Target. 11: 471-479
Holt-Harris, J E and Teague, O A (1916) J Infect Dis. 18: 596-600
Huybhebaert, N et al., (2005) Eur J Pharm Biopharm. 60: 349-359
Ingham et al. (2003) J Antimicrob Chemother. 51: 1365-1371
Ingham, et al. (2005) J Appl Microbiol. 98: 676-683
Jack, R W et al. (1995) Microbiol Rev. 59: 171-200
Kaldhusdal, M. (1999) FEMS Immunol Med Microbiol. 24: 337-343
Kimoto, H et al., (2004) Microbiol Immunol. 48: 75-82
Kondo, F. (1988). Res Vet Sci. 45: 337-340
Liu J R et al. (2005) Appl Environ Microbiol. 71: 6769-6775
MacConkey, A (1905) J Hyg. 8: 333-379
Medina, E et al., (2001) Vaccine. 19: 1573-1580
Mergulhao F J M et al (2005) Biotechnology Advances. 23: 177-202
Nahashon, S N et al. (1994) Poult Sci. 73: 1552-1562
Önöz, E and Hoffinan, K (1978) Zentralbl Bakteriol. 240: 16-21
Palacios M C et al. (2005) J Appl Microbiol. 98: 229-237
Prakash, S and Jones, M L (2005). J Biomed Biotechnol. 1: 44-56.
Roland, K L et al. (2005) Curr Opin Mol Ther. 7: 62-72
Soravia, E et al., (1988) FEBS Lett. 228: 337-340
Steidler, L. (2002) Antonie Van Leeuwenhoek. 82: 323-331
Steidler, L et al., (2003) Nat Biotechnol. 21: 785-789
Tacket, C O et al. (1992) Vaccine. 10: 443-6
Tagg, J R et al. (1976) Bacteriol Rev. 40: 722-756
Taylor, W J (1965) Am J Clin Path. 44: 471-475
Tschirdewahn, B et al. (1991) Int J Food Microbiol. 14: 175-178
Vohra, A and Satyanarayana, T (2003) Crit Rev Biotechnol. 23: 29-60
Watkins, K L et al. (1997) Vet Microbiol. 54: 195-200
Zhu, C. et al., (2006) Vaccine. 24: 3821-31

The invention claimed is:

1. An isolated colonising non-pathogenic Gram negative bacterium selected from CCEC22 as deposited with the National Measurement Institute (formerly AGAL) under accession number NM05/45635, CCEC31 as deposited with the National Measurement Institute (formerly AGAL) under accession number NM05/45636 or CCEC59 as deposited with the National Measurement Institute (formerly AGAL) under accession number NM05/45637.

2. The Gram negative bacterium of claim 1 which is modified to express one or more heterologous biologically active polypeptides.

3. The Gram negative bacterium of claim 1, wherein the bacterium is marked with a selectable marker.

4. The Gram negative bacterium of claim 1, wherein the bacterium colonises a mucosal surface of the subject.

5. The Gram negative bacterium of claim 1, wherein one or more of the biologically active polypeptides is a cytokine, hormone, enzyme, antimicrobial peptide, anti-tumour agent, enzyme, antibody or antigen.

6. The Gram negative bacterium of claim 2, wherein the bacterium is CCEC22 as deposited with the National Measurement Institute (formerly AGAL) under accession number NM05/45635.

7. The Gram negative bacterium of claim 2, wherein the bacterium is CCEC31 as deposited with the National Measurement Institute (formerly AGAL) under accession number NM05/45636.

8. The Gram negative bacterium of claim 2, wherein the bacterium is CCEC59 as deposited with the National Measurement Institute formerly AGAL) under accession number NM05/45637.

9. A method of delivering one or more heterologous biologically active polypeptides to a subject, the method comprising administering to the subject the colonising non-pathogenic Gram negative bacterium of claim 2.

10. The method of claim 9, wherein the bacterium is marked with a selectable marker.

11. The method of claim 9, wherein the subject is avian.

12. The method of claim 9, wherein the bacterium colonises a mucosal surface of said subject.

13. The method of claim 9, wherein one or more of the biologically active polypeptides is a cytokine, hormone, antimicrobial peptide, anti-tumour agent, enzyme, antibody or antigen.

14. The method of claim 9, wherein the Gram negative bacterium is administered orally to the subject.

15. The method of claim 9, wherein the method comprises administering to the subject the isolated colonising non-pathogenic Gram negative bacterium CCEC22 as deposited with the National Measurement Institute (formerly AGAL) under accession number NM05/45635 which has been modified to express one or more heterologous biologically active polypeptides.

16. The method of claim 9, wherein the method comprises administering to the subject the isolated colonising non-pathogenic Gram negative bacterium CCEC31 as deposited with the National Measurement Institute (formerly AGAL) under accession number NM05/45636 which has been modified to express one or more heterologous biologically active polypeptides.

17. The method of claim 9, wherein the method comprises administering to the subject the isolated colonising non-pathogenic Gram negative bacterium CCEC59 as deposited with the National Measurement Institute (formerly AGAL) under accession number NM05/45637 which has been modified to express one or more heterologous biologically active polypeptides.

* * * * *